(12) United States Patent
Rojas-Chapana et al.

(10) Patent No.: US 6,767,522 B1
(45) Date of Patent: Jul. 27, 2004

(54) METHOD FOR LEACHING SULFIDE-CONTAINING MATERIALS WITH MICROORGANISMS AND USE OF SULPHUR-CONTAINING AMINO ACIDS IN LEACHING WITH MICROORGANISMS

(75) Inventors: José Rojas-Chapana, Berlin (DE); Helmut Tributsch, Berlin (DE)

(73) Assignee: Hahn-Meitner-Institut Berlin GmbH, Berlin (DE)

( * ) Notice: Subject to any disclaimer, the term of this patent is extended or adjusted under 35 U.S.C. 154(b) by 0 days.

(21) Appl. No.: 09/744,809

(22) PCT Filed: Jul. 23, 1999

(86) PCT No.: PCT/EP99/05272

§ 371 (c)(1),
(2), (4) Date: Apr. 13, 2001

(87) PCT Pub. No.: WO00/06785

PCT Pub. Date: Feb. 10, 2000

(30) Foreign Application Priority Data

Jul. 30, 1998 (DE) .......................... 198 36 078

(51) Int. Cl.⁷ ........................... C01G 3/00; C01G 7/00; C01G 49/00
(52) U.S. Cl. ................................ 423/27; 423/DIG. 17; 423/150.1; 423/153; 435/262
(58) Field of Search .......................... 423/DIG. 17, 27, 423/150.1, 153; 435/243, 262

(56) References Cited

U.S. PATENT DOCUMENTS

| | | | |
|---|---|---|---|
| 2,829,964 A | | 4/1958 | Zimmerly et al. |
| 4,293,333 A | * | 10/1981 | Drobot .................. 423/DIG. 7 |
| 5,021,088 A | * | 6/1991 | Portier ................ 423/DIG. 17 |
| 5,413,624 A | | 5/1995 | Rusin et al. |

FOREIGN PATENT DOCUMENTS

DE 2901733 C2 5/1982
EP 0808910 A2 11/1997

OTHER PUBLICATIONS

Wenberg, et al., "Leaching of copper by fungi" Trans. Soc. Mining Eng., AIME, 250(3), pp. 207–212, Sep., 1971.*
Liu, et al., "Experimental studies on leaching of copper and gold by amino acids" Chin. Sci. Bull., 39(18), pp. 1541–1544, Sep. 1994.*
Duncan et al., "Leaching of Chalcopyrite with Thiobacillus ferrooxidans: Effect of Surfactants and Shaking," Applied Microbiology, vol. 12 (1964), No. 2, p. 122–126, Mar.
Ennaoui et al., "Iron disulfide for solar energy conversion," Solar Energy Materials and Solar Cells, vol. 29 (1993), pp. 289–370, no month.
Palencia et al., "Influence of Block Copolymers on the Microbiological Leaching of Pyrites by Discontinuous Operation," Tenside Detergents, vol. 21 (1984), pp. 90–93, no month.
Tuovinen et al., "Studies on the Growth of Thiobacillus ferroxidans," Arch. Mikrobiol., vol. 88 (1973), pp. 285–298.
Wakao et al., "Bacterial Pyrite Oxidation III. Adsorption of Thiobacillus Ferrooxidans cells on Solid Surfaces and its Effect on Iron Release from Pyrite," J. Gen. Appl. Microbiol., vol. 30 (1984), pp. 63–77, no month.
Tuovinen et al., Archives of Microbiology, vol. 105, No. 2, pp. 40–43 (1975), no month.

* cited by examiner

*Primary Examiner*—Steven Bos
(74) *Attorney, Agent, or Firm*—Norris McLaughlin & Marcus PA

(57) ABSTRACT

The invention relates to an effective and environmentally safe process for the microbial leaching of sulfidic materials, particularly of sulfide ores such as pyrite, marcasite, chalcopyrite, bornite, or covelline, which process is characterized in that the aqueous leaching fluid is added with sulfur-containing amino acids or derivatives thereof. The invention is also directed to the use of sulfur-containing amino acids or derivatives thereof in the microbial leaching of sulfidic materials, particularly in pyrite leaching.

13 Claims, 1 Drawing Sheet

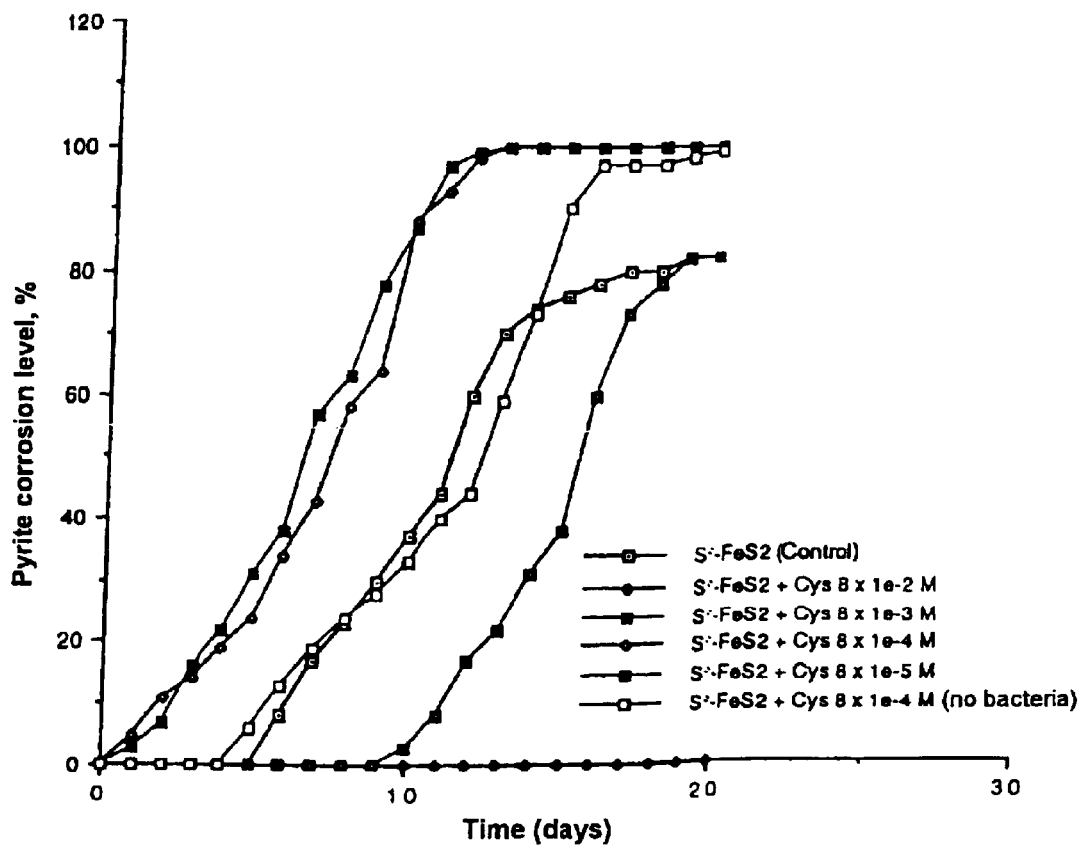
Fig. 1: Relationship between bacterial pyrite corrosion, cysteine concentration, and exposition period.

METHOD FOR LEACHING SULFIDE-CONTAINING MATERIALS WITH MICROORGANISMS AND USE OF SULPHUR-CONTAINING AMINO ACIDS IN LEACHING WITH MICROORGANISMS

This application is the national phase under 35 U.S.C. §371 of PCT International Application No. PCT/EP99/05272 which has an International filing date of, Jul. 23, 1999, which designated the United States of America.

The invention relates to an effective and environmentally safe process for the microbial leaching of sulfidic materials, particularly of sulfide ores such as pyrite, marcasite, chalcopyrite, bornite, or covelline, which process is characterized in that the aqueous leaching fluid is added with sulfur-containing amino acids or derivatives thereof. The invention is also directed to the use of sulfur-containing amino acids or derivatives thereof in the microbial leaching of sulfidic materials, particularly in pyrite leaching.

Microbial leaching is a well-known process in biohydrometallurgy for leaching out metals from ores and other mineral raw materials through the action of microorganisms. Obligatorily chemolithoautotrophic Thiobacillus species such as *T. ferrooxidans* and *T. thiooxidans* whose energy sources are sulfides, elemental sulfur and soluble thiosulfates, but also iron(II) ions as an alternative, play a central role in the chemistry of ore leaching. In any case, the microbial action leads up to the sulfate. As an example, reference is made to U.S. Pat. No. 2,829,964 wherein a cyclic leaching process using iron-oxidizing bacteria is described. In this process, the ore is leached with a sulfuric Fe(III) sulfate solution obtained using bacteria. Thereafter, leach and gangue are separated, the leach metal content is extracted, and the Fe(II)-containing final leach is re-oxidized using bacteria.

The literature also suggests a number of processes to improve ore leaching and, in particular, to increase the leaching rate, which processes, above all, envisage the use of surface-active substances (D. W. Duncan, P. C. Trussell, and C. C. Walden, Leaching of Chalcopyrite with *Thiobacillus ferrooxidans*: Effect of Surfactants and Shaking, 1964, Applied Microbiology 12(2), 122–126; I. Palencia, F. Carranza, and J. Pereda, Influence of Block Copolymers on the Microbiological Leaching of Pyrites by Discontinuous Operation, 1984, Tenside Detergents 21(2), 90–93; N. Wakao, M. Mishina, Y. Sakurai, and H. Shiota, Bacterial Pyrite Oxidation III. Adsorption of *Thiobacillus ferrooxidans* Cells on Solid Surfaces and Its Effects on Iron Release from Pyrite, 1984, J. Gen. Appl. Microbiol. 30, 63–67).

It is believed that these substances—chiefly surfactants or polysaccharides and peptides or proteins—improve the contact between bacteria and sulfide, thereby facilitating bacterial attack.

However, the surfactants that are used are disadvantageous because they have lacking or low biodegradability and do not represent environmentally safe substances. Peptides and proteins as surface-active compounds exhibit controversial effects in the leaching process.

It was therefore the object of the present invention to provide an effective leaching process with improved dissolution rate without the use of environmentally hazardous additives.

Surprisingly, it has now been found that bacterial attack by Thiobacillus species on sulfidic materials can be greatly accelerated by adding the aqueous leaching fluid with an amino acid, selected from cysteine, methionine, or derivatives thereof, or a mixture of these compounds at low concentration.

More specifically, homocysteine and amides or esters of cysteine, methionine or homocysteine are possible as derivatives which can be used in the leaching process according to the invention. Homocysteine is a derivative of methionine wherein the methyl group on the sulfur has been replaced by hydrogen, so that homocysteine—like cysteine—has a sulfhydryl group. According to the invention, both racemates and optically active forms of the amino acids may find use.

It has been found that an optimum effect is achieved in those cases where the concentration of the added amino acid(s) or derivatives thereof in the aqueous leaching fluid is low, not exceeding $8 \times 10^{-3}$ M, in particular. Concentrations of from $8 \times 10^{-4}$ to $8 \times 10^{-5}$ M are particularly preferred. The pH value of the leaching fluid is adjusted to 1.0–4.0, preferably to 1.5–2.0, and more preferably to 1.6. Adjustment is effected using suitable buffer solutions, e.g. Tuovinen buffer (Arch. Mikrobiol, 88, 285–298 (1973)).

According to the invention, there are two possible ways of performing the leaching process. On the one hand, the leaching fluid may include both the Thiobacillus species and the sulfur-containing amino acids or derivatives thereof. This embodiment is the preferred one. Alternatively, it is also possible to use the dilute amino acid solution alone as leaching fluid and subsequently add the thiobacilli to the discharging fluid (e.g. outside the dump) which is recycled. These two possible ways do not exclude the principal methods of ore leaching well-known to those skilled in the art, i.e., slope leaching, dump leaching or in situ leaching. In practice, the process according to the invention can be used with any of the three ore leaching processes.

According to the invention, *T. ferrooxidans* is preferred as Thiobacillus species. This strain is acidophilic, occurring in acidic waters of ore mines. Detailed investigations relating to the growth of this strain have also been described by Tuovinen O. H. et al. in Arch. Mikrobiol. 88, 285–298 (1973).

Thus, the process of the invention provides an effective method of ore leaching, particularly of pyrite, which process, in contrast to current methods such as cyanide leaching, does not represent any risk for the ecological balance of the environment. The amino acids and their derivatives used according to the invention are environmentally safe and inexpensive starting materials. They are employed at exceedingly low concentrations and result in an essential improvement of bacterial dissolution of metal sulfides (e.g. $FeS_2$). Thus, for example, the process according to the invention permits speeding up the microbial recovery of copper or gold from pyrite ores.

The invention is also directed to the novel use of sulfur-containing amino acids, derivatives or mixtures thereof in the microbial leaching of sulfidic materials, particularly of sulfide ores.

With reference to the embodiments, the invention will be illustrated in more detail below.

EXAMPLE 1

Preparation of Pyrite Layers Using a Low-pressure MOCVD Plant (Metal-organic Chemical Vapor Deposition)

The metal-organic chemical vapor deposition (MOCVD) is a process for preparing thin polycrystals and epitaxial layers, said layers being deposited from the gaseous phase. Organometallic compounds are mostly used as starting materials (precursors). The deposition process proceeds as follows: A carrier gas is passed through so-called bubblers. The bubbler contains the organometallic compounds in liquid or solid form. As a result, the starting materials are taken up by the carrier gas. The starting compounds are passed over a heated substrate by the carrier gas. The starting compounds include the elements which are to form the layer. The compounds undergo decomposition over the substrate surface in a reaction. As a result, the elements contributing to layer formation are liberated. These elements attach to the substrate surface, thereby forming the layer. Excess decomposition products are conveyed to the vent air by the carrier gas. In the present Example, the pyrite layers are prepared using an MOCVD plant as described in "Solar Energy Materials and Solar Cells" 1993, 29, 289–370. Elemental sulfur was used as suitable sulfur precursor. In the preparation of pyrite, iron pentacarbonyl [$Fe(CO)_5$] was used as iron precursor.

EXAMPLE 2

Acceleration of Bacterial Dissolution of Pyrite Layers with *Thiobacillus ferrooxidans* in the Presence of Cysteine Each time, 1 $cm^3$ of pyrite layers 100 nm in thickness (referred to as $S°$-$FeS_2$), prepared according to Example 1 using elemental sulfur as precursor, was added with 300 $\mu l$ of aqueous solutions or suspensions of *Thiobacillus ferrooxidans* cells and cysteine at concentrations of from $8 \times 10^{-2}$ to $8 \times 10^{-5}$ M in an in situ pyrite culture chamber. The pH value of the solutions was adjusted to 1.6 using Tuovinen buffer (for 1 liter: $KH_2PO_4$=0.4 g, $MgSO_4.7H_2O$=0.4 g, $(NH_4)_2SO_4$=0.4 g, $FeSO_4.7H_2O$=33.3 g, with no iron(II) being added) [cf., Tuovinen and Kelly, Arch. Mikrobiol. 88, 285–298 (1973)].

FIG. 1 is a plot of the pyrite corrosion level (or dissolution rate) [%] as a function of time [days] for the various solutions. Clearly, the bacterial pyrite dissolution rate is highly accelerated in the presence of a sulfur-containing amino acid at concentrations below $8 \times 10^{-3}$ M. At concentrations of $8 \times 10^{-4}$ M and $8 \times 10^{-5}$ M cysteine in the solution, a lag phase no longer occurs, and a pyrite corrosion level of 100% is achieved after only 10–11 days.

What is claimed is:

1. A process for microbial leaching of a sulfidic material, the process comprises the steps of:
   a) preparing an aqueous leaching fluid consisting of
      at least one sulfur-containing amino acid selected from the group consisting of cysteine, methionine, and homocysteine; or an amide or ester thereof, and optionally a buffer;
   b) contacting said fluid with the sulfidic material for a length of time sufficient to achieve leaching,
   wherein bacteria of the genus Thiobacillus are either a component of the aqueous leaching fluid of step (a) or, the bacteria are added to a discharging fluid, wherein said discharging fluid comprises the aqueous leaching fluid resulting from the performance of step (b).

2. The process of claim 1 wherein the leaching fluid includes the bacteria.

3. The process of claim 1 wherein the bacteria are added to the discharging fluid.

4. The process of claim 1 wherein, the total concentration of the at least one sulfur-containing amino acid is equal to or less than $8 \times 10^{-3}$ M.

5. The process of claim 1 wherein the pH of the leaching fluid is between 1 and 4.

6. The process of claim 5, wherein the pH of the leaching fluid is between 1.5 to 2.

7. The process of claim 1, wherein the bacteria are *Thiobacillus ferrooxidans*.

8. The process of claim 1, wherein the sulfidic material comprises one or more sulfide ores.

9. The process of claim 1, wherein the leaching fluid consists of at least one amide or ester of a sulfur containing amino acid selected from the group of methionine, cysteine, and homocysteine, and optionally, a buffer.

10. The process of claim 1, wherein the sulfidic material is pyrite.

11. A process for microbial leaching of a sulfidic material, wherein the process comprises the steps of:
   a) preparing an aqueous leaching fluid consisting of
      at least one sulfur-containing amino acid selected from the group consisting of cysteine, methionine, and homocysteine; or an amide or ester thereof,
      bacteria of the genus Thiobacillus, optionally a buffer, and
   b) contacting said aqueous leaching fluid with the sulfidic material for a period of time sufficient to achieve leaching.

12. The process of claim 11, wherein the total concentration of the at least one sulfur-containing amino acid or the amide or ester thereof, is equal to or less than $8 \times 10^{-3}$ M.

13. The process of claim 11, wherein the leaching fluid consists of at least one amide or ester of a sulfur containing amino acid selected from the group of methionine, cysteine, and homocysteine.

* * * * *